United States Patent
Morris

(10) Patent No.: US 10,004,554 B2
(45) Date of Patent: Jun. 26, 2018

(54) ELECTROSURGICAL INSTRUMENT AND SYSTEM

(71) Applicant: GYRUS MEDICAL LIMITED, Cardiff (GB)

(72) Inventor: David Morris, Mid Glamorgan (GB)

(73) Assignee: GYRUS MEDICAL LIMITED, Cardiff (GB)

( * ) Notice: Subject to any disclaimer, the term of this patent is extended or adjusted under 35 U.S.C. 154(b) by 1002 days.

(21) Appl. No.: 14/281,087

(22) Filed: May 19, 2014

(65) Prior Publication Data

US 2014/0343547 A1 Nov. 20, 2014

(30) Foreign Application Priority Data

May 17, 2013 (GB) .................................. 1308901.6

(51) Int. Cl.
*A61B 18/18* (2006.01)
*A61B 18/14* (2006.01)
(Continued)

(52) U.S. Cl.
CPC .............................. *A61B 18/1402* (2013.01);
*A61B 2018/00577* (2013.01); *A61B 2018/00601* (2013.01);
(Continued)

(58) Field of Classification Search
CPC ...... A61B 18/1402; A61B 2018/00577; A61B 2018/00601; A61B 2018/00625;
(Continued)

(56) References Cited

U.S. PATENT DOCUMENTS

| 6,210,405 B1 | 4/2001 | Goble et al. |
| 6,482,202 B1 | 11/2002 | Goble et al. |
| 6,530,924 B1 * | 3/2003 | Ellman .............. A61B 18/1485 606/41 |

(Continued)

FOREIGN PATENT DOCUMENTS

| CN | 1222065 A | 7/1999 |
| GB | 1 449 081 | 9/1976 |
| WO | WO 2006/092565 A1 | 9/2006 |

OTHER PUBLICATIONS

Search Report issued in British Patent Application No. 1308901.6 dated Nov. 15, 2013.
Aug. 1, 2017 Office Action issued in Chinese Application No. 20140252428.5.

*Primary Examiner* — Michael Peffley
*Assistant Examiner* — Amanda Zink
(74) *Attorney, Agent, or Firm* — Oliff PLC

(57) ABSTRACT

An electrosurgical instrument includes an instrument shaft, a suction tube extending along the shaft, and a tissue treatment electrode at the distal end of the shaft. The tissue treatment electrode includes at least a first part and a second part, the first and second parts each having an outer section including mating surfaces adapted to form a close-fitting barrier when the first and second parts are mated one with another, such as to inhibit the passage of gas across the barrier. At least one of the parts also includes an inner section with a longitudinal recess so as to form a suction lumen when the first and second parts are mated one with another. The suction lumen is in fluid communication with the suction tube, the tissue treatment electrode also including one or more apertures in communication with the suction lumen.

18 Claims, 4 Drawing Sheets

(51) Int. Cl.
  *A61B 18/00* (2006.01)
  *A61B 18/16* (2006.01)

(52) U.S. Cl.
  CPC ........... *A61B 2018/00625* (2013.01); *A61B 2018/1412* (2013.01); *A61B 2018/162* (2013.01); *A61B 2218/008* (2013.01); *Y10T 29/49117* (2015.01)

(58) Field of Classification Search
  CPC ...... A61B 2018/1412; A61B 2018/162; A61B 2218/008
  See application file for complete search history.

(56) References Cited

U.S. PATENT DOCUMENTS

| | | | | |
|---|---|---|---|---|
| 6,896,674 | B1* | 5/2005 | Woloszko | A61B 18/1206 604/114 |
| 7,815,635 | B2* | 10/2010 | Wittkampf | A61B 18/1492 606/39 |
| 2001/0029394 | A1* | 10/2001 | Dobak, III | A61F 7/12 607/105 |
| 2002/0173776 | A1 | 11/2002 | Batchelor et al. | |
| 2013/0345661 | A1* | 12/2013 | Chang | A61B 17/3207 604/501 |

* cited by examiner

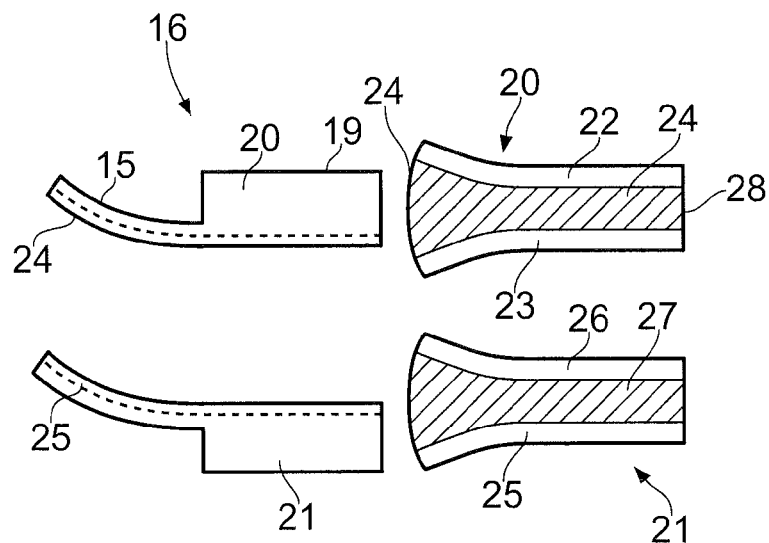
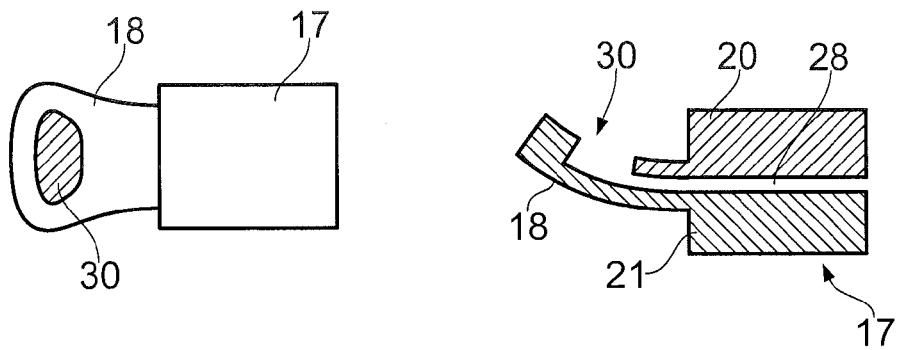
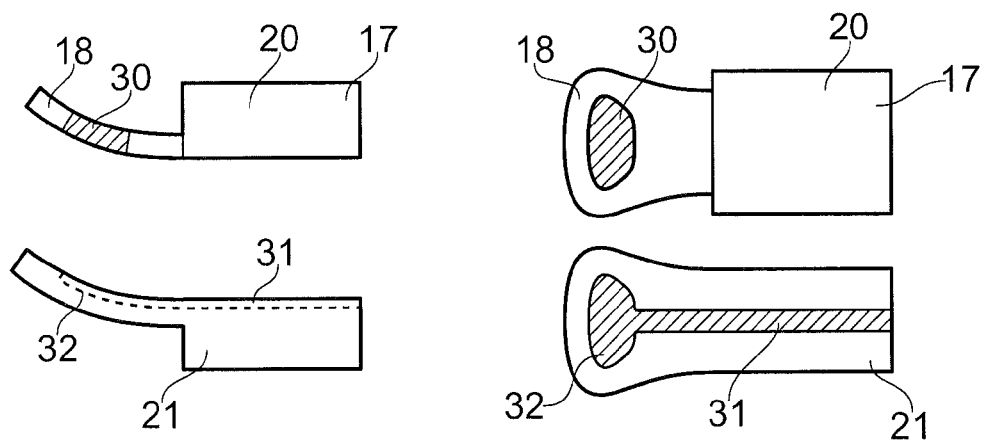
FIG. 6  FIG. 7
FIG. 8  FIG. 9
FIG. 10  FIG. 11

ELECTROSURGICAL INSTRUMENT AND SYSTEM

TECHNICAL FIELD

This invention relates to an electrosurgical instrument and to an electrosurgical system for the treatment of tissue. Such systems are commonly used for the vaporisation and/or coagulation of tissue in surgical intervention, most commonly in "keyhole" or minimally invasive surgery, but also in "open" surgery.

BACKGROUND TO THE INVENTION AND PRIOR ART

There is a frequent requirement during a surgical procedure for suction in order to remove matter from the surgical site, whether it is tissue debris, smoke, fluid, gas bubbles or other unwanted matter that interfere with the procedure or obscure the surgeon's view of the surgical site. U.S. Pat. Nos. 6,210,405 & 6,482,202 describe examples of this type of surgical instrument.

SUMMARY OF THE INVENTION

Embodiments of the invention provide a tissue treatment electrode that is formed from at least two parts that are brought together at respective mating surfaces to form the complete electrode. At least one of the respective mating surfaces has a channel formed therein that forms, when the parts are brought together, a suction lumen extending through the tissue treatment electrode from a tissue treatment surface thereof to an output port that in use is in fluid communication with a suction tube of an electrosurgical instrument. In some embodiments respective channels may be formed in both (or more) parts, located such that when the parts are brought together the channels are co-located so as to form as single, larger suction lumen. The advantage of the multi-construction is that separate parts having grooves or channels formed into the surface thereof that may then be brought together into a complete electrode are easier to fabricate than solid one-piece electrodes having suction lumens formed therein.

Accordingly, an electrosurgical instrument is provided for the treatment of tissue, the instrument comprising an instrument shaft, a suction tube extending along the shaft, and a tissue treatment electrode at the distal end of the shaft, the tissue treatment electrode comprising at least first and second parts, the first and second parts each comprising an outer section including mating surfaces adapted to form a close-fitting barrier when the first and second parts are mated one with another, such as to inhibit the passage of gas across the barrier, the outer section of at least one of the parts having an exposed surface for treating tissue, at least one of the parts also including an inner section with a longitudinal recess so as to form a suction lumen when the first and second parts are mated one with another, the suction lumen being in fluid communication with the suction tube, the tissue treatment electrode also including one or more apertures in communication with the suction lumen such that suction applied to the suction tube causes material adjacent the one or more apertures to be transferred into the suction lumen and then the suction tube for removal.

In this way, when the first and second parts come together with their mating surfaces forming a barrier to the passage of gas across the mating surfaces, the recess forms a suction lumen through the electrode for the evacuation of tissue debris, smoke, fluid, gas bubbles or other unwanted matter. Where the electrode is particularly small or of a convoluted shape, it may be preferable to form the suction lumen in this way as opposed to trying to form a unitary solid electrode and then remove material to form a suction lumen. While it may be preferable for the barrier formed by the mating surfaces to constitute a gas-tight seal, it is not necessary for it to be completely gas-tight, as long as it inhibits the flow of gasses across the barrier sufficiently for the majority of the gas flow to be longitudinally along the suction lumen.

Preferably, the instrument also includes a return electrode which is electrically insulated from the tissue treatment electrode by means of an insulation member. The tissue treatment electrode therefore forms the active electrode in a bipolar electrode assembly, with the advantages in terms of control and safety associated with bipolar electrosurgery.

Whether the tissue treatment electrode is a monopolar electrode or part of a bipolar electrode assembly, the one or more apertures are conveniently present in the exposed surface for treating tissue. Thus, the debris or other material is evacuated from the very region where tissue treatment is taking place.

According to one convenient arrangement, the tissue treatment electrode is shaped so as to provide a narrow blade-like portion. Such blade-like electrodes provide very precise and effective tissue cutting, but it is difficult to provide effective suction unless the arrangement of the present invention is employed. The tissue treatment electrode is conveniently substantially chisel-shaped.

The one or more apertures may be formed separately from the suction lumen and arranged to be in fluid communication therewith, or alternatively the one or more apertures may be formed by the longitudinal recess extending all the way to the outer surface of the electrode. If the longitudinal recess extends to the surface of one of the parts, the end of the recess constitutes the one or more apertures. The recess may change in diameter to form an elongate aperture, or conveniently may split to form multiple apertures. Conveniently, the one or more apertures are present at the distal end of the tissue treatment electrode. Where the tissue treatment electrode is a chisel-shaped electrode, this ensures that the suction is provided at the distal tip of the chisel blade, exactly where the majority of the tissue treatment is likely to take place.

Alternatively, the one or more apertures are conveniently present on a side face of the tissue treatment electrode. This allows for a "side-effect" instrument to be provided, in which the tissue is treated laterally of the electrode, allowing for good visualisation of the surgical site. Where the tissue treatment electrode is shaped so as to provide a narrow blade-like portion, at least one of the one or more apertures is present on the side face of the blade-like portion. This once again allows for suction to be provided where the majority of the tissue treatment is likely to take place.

In one convenient arrangement, the instrument includes a plurality of apertures disposed radially around the tissue treatment electrode. In this way suction is provided in all directions around the tissue treatment electrode, such that debris can be evacuated however it is disposed with regard to the electrode.

The recess forming the suction lumen is not necessarily present in only one of the first and second parts. According to a convenient arrangement both the first and second parts are provided with an inner section with a longitudinal recess so as to form the suction lumen. Thus the suction lumen is formed by the combination of the recesses in both parts, for example by a semicircular groove in each part forming a cylindrical lumen once the first and second parts are mated together.

The instrument conveniently includes connection means for connecting the first and second parts one to the other. This connection means is conceivably mechanical, for example a mechanical connection between the tissue treatment electrode and the shaft. Alternatively, the connection means conceivably comprises an additional component such as an adhesive, or the first and second parts are connected one to the other by means of a weld, or by means of diffusion bonding.

Embodiments of the invention further reside in a tissue treatment electrode for the treatment of tissue, the tissue treatment electrode comprising at least first and second parts, the first and second parts each comprising an outer section including mating surfaces adapted to form a close-fitting barrier when the first and second parts are mated one with another, such as to inhibit the passage of gas across the barrier, the outer section having an exposed surface for treating tissue, at least one of the parts also including an inner section with a longitudinal recess so as to form a suction lumen when the first and second parts are mated one with another, the tissue treatment electrode also including one or more apertures in communication with the suction lumen such that suction applied to the suction lumen causes material adjacent the one or more apertures to be transferred into the suction lumen for removal.

Another embodiment further extends to a method of forming a tissue treatment electrode for the treatment of tissue, comprising the steps of a) forming first and second parts, each comprising an outer section including mating surfaces, at least one of the first and second parts also having an exposed surface for treating tissue, at least one of the parts also having one or more apertures, at least one of the parts also including an inner section with a longitudinal recess, b) connecting the first and second parts one to the other such that the mating surfaces form a close-fitting barrier such as to inhibit the passage of gas therethrough, and the longitudinal recess forms a suction lumen, such that suction applied to the suction lumen causes material adjacent the one or more apertures to be transferred into the suction lumen for removal.

BRIEF DESCRIPTION OF THE DRAWINGS

Embodiments of the invention will now be further described, by way of example only, with reference to the accompanying drawings, in which:

FIG. 6 is an exploded side view of the tip of FIG. 2, FIG. 7 is an exploded plan view of the tip of FIG. 2, FIG. 8 is a plan view of a tip in accordance with an alternative embodiment of the invention, FIG. 9 is a sectional side view of the tip of FIG. 8, FIG. 10 is an exploded side view of the tip of FIG. 8, FIG. 11 is an exploded plan view of the tip of FIG. 8.

DESCRIPTION OF THE EMBODIMENTS

Figure 1:
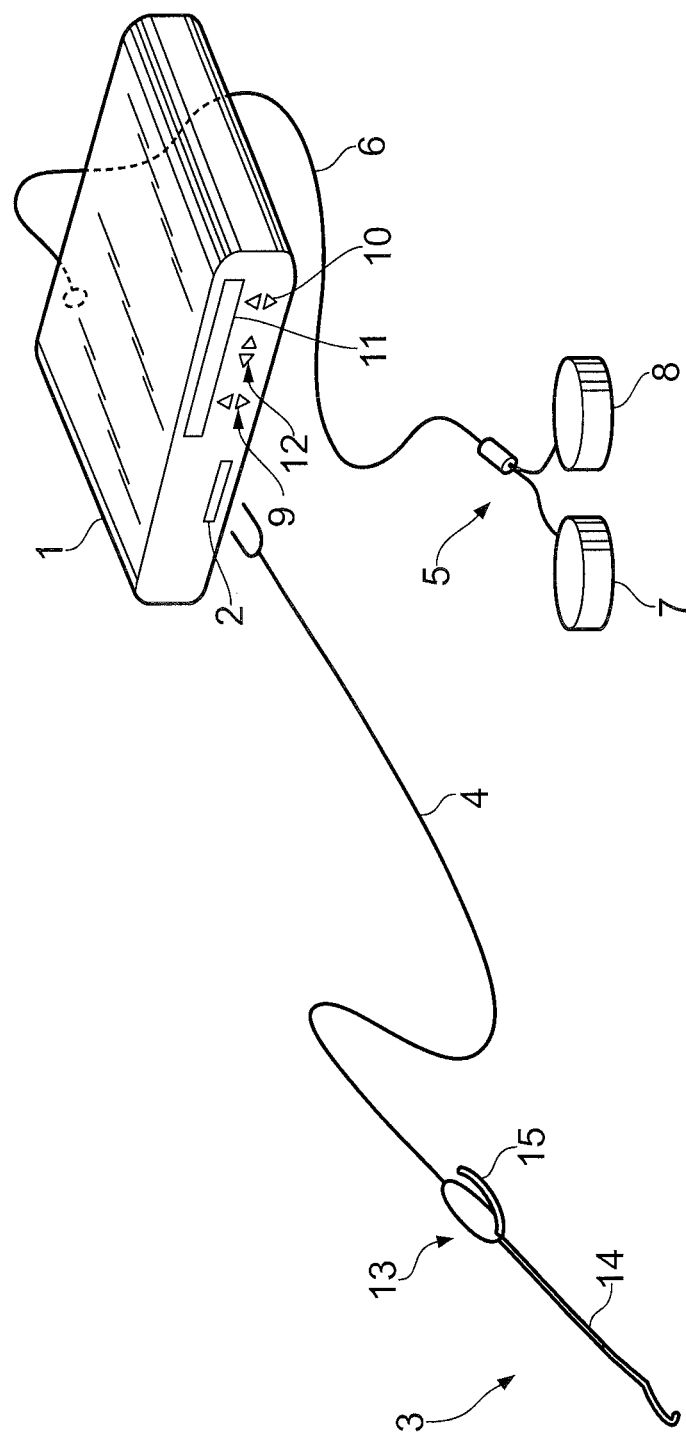
FIG. 1 is a schematic diagram of an electrosurgical system using an electrosurgical instrument in accordance with an embodiment of the present invention.

Referring to the drawings, FIG. 1 shows electrosurgical apparatus including a generator 1 having an output socket 2 providing a radio frequency (RF) output, via a connection cord 4, for an electrosurgical instrument 3. Activation of the generator 1 may be performed from the instrument 3 via a handswitch (not shown) on the instrument 3, or by means of a footswitch unit 5 connected separately to the rear of the generator 1 by a footswitch connection cord 6. In the illustrated embodiment, the footswitch unit 5 has two footswitches 7 and 8 for selecting a desiccation mode and a vaporisation mode of the generator 1 respectively. The generator front panel has push buttons 9 and 10 for respectively setting desiccation and vaporisation power levels, which are indicated in a display 11. Push buttons 12 are provided as an alternative means for selection between the desiccation and vaporisation modes.

The electrosurgical instrument 3 comprises a housing 13 with an elongate shaft 14, and tissue treatment electrodes at the distal end of the shaft, as will be described below. A movable handle 15 associated with the housing can be actuated to cause the shaft to bend. This instrument is particularly suited to the treatment of the hip joint, where a relatively long shaft with articulation capability is needed to access the area to the treated.

Figure 2:
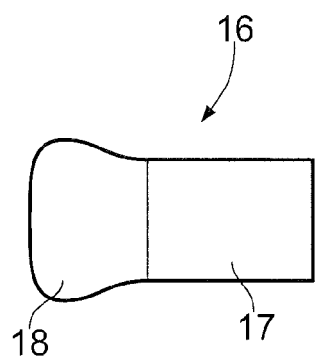
FIG. 2 is a plan view of the tip of an electrosurgical instrument in accordance with an embodiment of the present invention and capable of being used in the system of FIG. 1.
Figure 3:
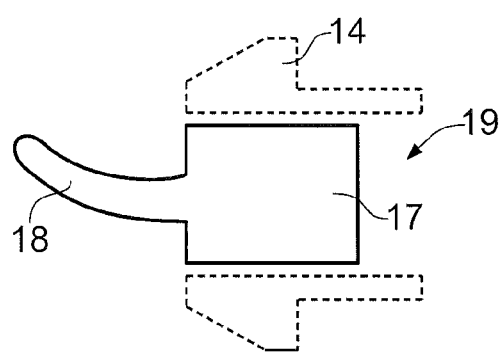
FIG. 3 is a side view of the tip of FIG. 2, with a part of the shaft of the instrument shown in section.

FIGS. 2 & 3 show a tissue treatment electrode 16 comprising a body portion 17 and a blade portion 18. The blade portion 18 extends forwardly from the body portion 17 in the form of a chisel. The electrode 16 is positioned within the elongate shaft 14, adjacent a suction tube 19.

Figure 4:
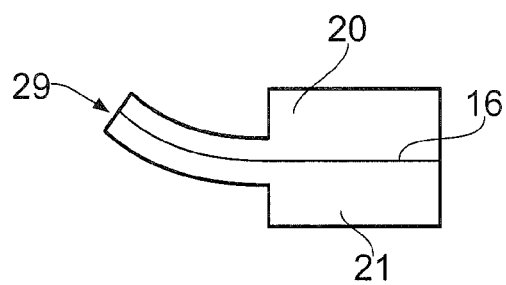
FIG. 4 is a side view of the tip of FIG. 2.
Figure 5:
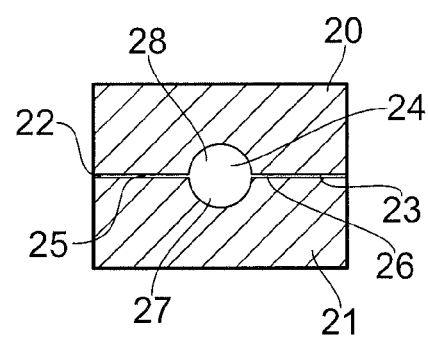
FIG. 5 is a cross-sectional end view of the tip of FIG. 2.
Figure 12:
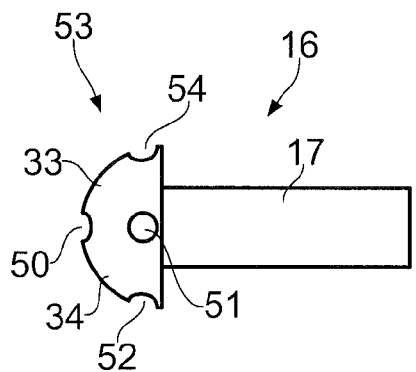
FIG. 12 is a side view of a tip in accordance with a further embodiment of the invention.
Figure 13:
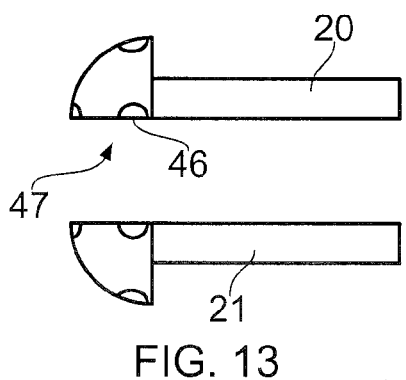
FIG. 13 is an exploded side view of the tip of FIG. 12.
Figure 14:
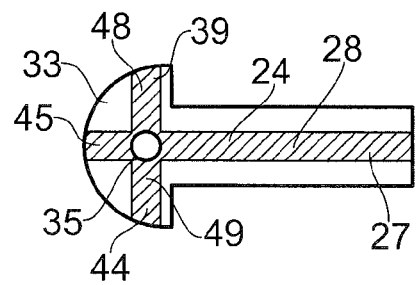
FIG. 14 is a sectional side view of the tip of FIG. 12.
Figure 15:
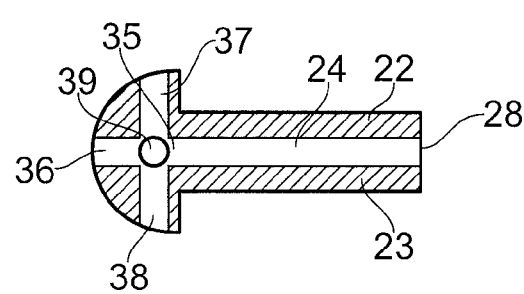
FIG. 15 is a sectional plan view of the tip of FIG. 12 shown from below.
Figure 16:
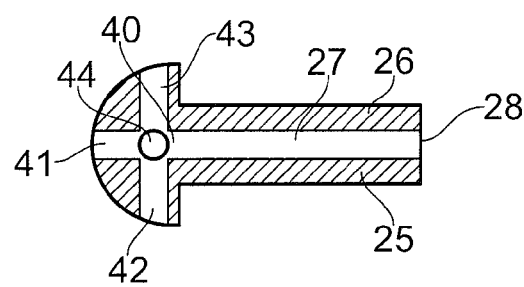
FIG. 16 is a sectional plan view of the tip of FIG. 12 shown from above.

The electrode 16 is formed of an upper part 20 and a lower part 21, as shown in FIG. 4. FIG. 5 shows a cross-sectional view of the upper part 20 and lower part 21, and shows how the upper part 20 has mating faces 22 & 23 on each side of a longitudinal recess 24. Similarly, the lower part 21 has corresponding mating faces 25 & 26 on each side of a longitudinal recess 27. When the upper and lower parts are registered one against the other, with the mating faces 22 & 25 in abutment on one side and the mating faces 23 & 26 in abutment on the other side, the recesses 24 & 27 combine to form a cylindrical suction lumen 28. The lumen extends through the body portion 17 and the blade portion 18 to exit the blade portion at an external aperture 29. The recesses 24 & 27 increase in width throughout the blade portion 18 so that the aperture 29 is in the form of a slot, as shown in FIGS. 6 & 7.

The upper and lower parts 20 & 21 are held in position within the shaft 14 by the use of an adhesive, or alternatively by means of a welded joint. A lead (not shown) connects the electrode 16 to the electrosurgical generator 1, so that it can act either as a monopolar tissue treatment electrode or as part of a bipolar electrosurgical assembly in combination with a return electrode (not shown). The instrument 3 is connected to a source of suction (not shown) such that suction is provided at the proximal end of the suction tube 19. Tissue debris, smoke, fluid, gas bubbles or other unwanted matter can be evacuated from the surgical site through the aperture 29, into the suction lumen 28 and into the suction tube 19, to be removed through the proximal end of the instrument.

FIGS. 8 to 11 show an alternative electrode 16 in which the body portion 17 and blade portion 18 are arranged as before, but other features are arranged differently. Firstly, the upper part 20 does not contain a longitudinal recess, but only an aperture 30 extending laterally through the blade portion 18. The lower part 21 does contain a longitudinal recess 31, but the recess 31 does not extend all the way to the distal end of the blade portion 18, instead terminating in a bowl-shaped chamber 32 situated adjacent the aperture 30. The upper and lower parts 20 & 21 can be registered one against the other in a similar manner to that previously described, with mating faces 22 & 25 in abutment and the mating faces 23 & 26 in abutment. The recess 31, chamber 32 and aperture 30 together constitute a suction lumen 28 extending along the electrode 16 and exiting the electrode on the upper surface of the blade portion 18. When in use and connected to the generator 1 and to a source of suction, tissue debris and other material can be evacuated from the surgical site adjacent the blade portion 18, via the suction lumen 28 and suction tube 19.

FIGS. 12 to 16 show a further electrode 16 which has a body portion 17 as before, but instead of a blade portion the electrode of FIGS. 12 to 15 has a button portion 33. The button portion 33 comprises an enlarged head, with a semi-spherical external surface 34. As before, the electrode 16 is constituted by an upper part 20 and a lower part 21, each part having mating faces 22 & 23 and 25 & 26 as previously described, with longitudinally extending recesses 24 & 27. The recesses on the upper part 20 are provided with a junction point 35, at which point the recess 24 splits into a forward recess 36, first side recess 37 and an opposite side recess 38. A borehole 39 extends orthogonally from the junction point 35 through the button portion 33. Similarly, the lower part 21 has a junction point 40, with a corresponding forward recess 41, first side recess 42 and opposite side recess 43. A borehole 44 extends orthogonally from the junction point 40 through the button portion 33.

When the upper and lower parts 20 & 21 are registered one against the other, the recesses 24 & 27 constitute a cylindrical suction lumen 28, while the recesses 36 & 41 constitute a forward passage 45, the first side recesses 37 & 42 constitute a first side passage 46, and the opposite side recesses 38 & 43 constitute an opposite side passage 47. The boreholes 39 and 44 constitute upper and lower passages 48 & 49. The passages 45 to 49 each extend to the surface of the button portion, so as to constitute apertures 50 to 55. Thus, in total, the upper and lower parts 20 & 21 provide a semi-spherical external surface with a forward aperture 50, and side apertures 51 to 55 disposed at regular 90 degree intervals around the circumference of the button portion 33.

This electrode 16 provides a relatively large and smooth external surface 34, but with apertures leading to a central suction lumen from various positions around the electrode. In use, when the electrode is connected to the electrosurgical generator 1 and to a source of suction, tissue debris and other material can be evacuated from the surgical site through any of the various apertures 50 to 55, into the passages 45 to 49, into the suction lumen 28 and hence removed through the proximal end of the instrument 3.

The instrument 3 is primarily designed to be operated in a conductive fluid such as saline, with the fluid completing the circuit between the electrodes. However, the instrument 3 can also be used as a dry-field instrument, in which case the user must ensure that the electrode or electrodes are placed in contact with the tissue to be treated.

Alternative embodiments will be envisaged by those skilled in the art without departing from the scope of the present invention. For example, the number and spacing of the passages and apertures described above can be varied depending on the required electrode geometry. However, the provision of an electrode constituted by two or more parts with one or more recesses which come together to form a suction lumen within the electrode allows for the design of relatively small and complex electrodes in which it would be difficult to form an integral suction lumen by any other method.

The invention claimed is:

1. An electrosurgical instrument for the treatment of tissue, the instrument comprising:
   an instrument shaft;
   a suction tube extending along the shaft; and
   a tissue treatment electrode at the distal end of the shaft,
   the tissue treatment electrode comprising at least first and second parts, the first and second parts each comprising an outer section including mating surfaces adapted to form a close-fitting barrier when the first and second parts are mated one with another, such as to inhibit the passage of gas across the barrier, the outer section of at least one of the parts having an exposed surface for treating tissue, at least one of the parts also including an inner section with a longitudinal recess so as to form a suction lumen when the first and second parts are mated one with another, the suction lumen being in fluid communication with the suction tube,
   the tissue treatment electrode also including one or more apertures in communication with the suction lumen such that suction applied to the suction tube causes material adjacent the one or more apertures to be transferred into the suction lumen and then the suction tube for removal,
   wherein the mating surfaces are transversely extending.

2. The electrosurgical instrument according to claim 1, wherein the instrument also includes a return electrode which is electrically insulated from the tissue treatment electrode by means of an insulation member.

3. The electrosurgical instrument according to claim 1, wherein the longitudinal recess extends to the surface of at least one of the parts so as to form the one or more apertures.

4. The electrosurgical instrument according to claim 1, wherein the one or more apertures are present in the exposed surface.

5. The electrosurgical instrument according to claim 1, wherein the tissue treatment electrode is shaped so as to provide a narrow blade-like portion.

6. The electrosurgical instrument according to claim 5, wherein the tissue treatment electrode is substantially chisel-shaped.

7. The electrosurgical instrument according to claim 5, wherein at least one of the one or more apertures is present on the side face of the blade-like portion.

8. The electrosurgical instrument according to claim 1, wherein the one or more apertures are present at the distal end of the tissue treatment electrode.

9. The electrosurgical instrument according to claim 1, wherein the one or more apertures are present on a side face of the tissue treatment electrode.

10. The electrosurgical instrument according to claim 1, wherein the instrument includes a plurality of apertures disposed radially around the tissue treatment electrode.

11. The electrosurgical instrument according to claim 1, wherein the mating surfaces transversely extend in the longitudinal direction of the suction lumen.

12. The electrosurgical instrument according to claim 1, wherein both the first and second parts are provided with an inner section with a longitudinal recess so as to form the suction lumen.

13. The electrosurgical instrument according to claim 1, including connection means for connecting the first and second parts one to the other.

14. The electrosurgical instrument according to claim 13, wherein the connection means comprises a mechanical connection between the tissue treatment electrode and the shaft.

15. The electrosurgical instrument according to claim 13, wherein the connection means comprises an adhesive.

16. The electrosurgical instrument according to claim 13, wherein the connection means comprises a weld.

17. A tissue treatment electrode for the treatment of tissue, the tissue treatment electrode comprising at least first and second parts, the first and second parts each comprising an outer section including mating surfaces adapted to form a close-fitting barrier when the first and second parts are mated one with another, such as to inhibit the passage of gas across the barrier, the outer section having an exposed surface for treating tissue,
   at least one of the parts also including an inner section with a longitudinal recess so as to form a suction lumen when the first and second parts are mated one with another, the tissue treatment electrode also including one or more apertures in communication with the suction lumen such that suction applied to the suction lumen causes material adjacent the one or more apertures to be transferred into the suction lumen for removal,
   wherein the mating surfaces are transversely extending.

18. The electrosurgical instrument according to claim 12, wherein the suction lumen is formed only when the first and second parts are mated with each other, and
   wherein the suction lumen is not formed when the first and second parts are not mated with each other.

* * * * *